(12) United States Patent
Clement et al.

(10) Patent No.: US 8,926,673 B2
(45) Date of Patent: Jan. 6, 2015

(54) VERTEBRAL ARTHRODESIS EQUIPMENT

(75) Inventors: Jean Luc Clement, La Colle sur Loup (FR); Vincent Fiere, Lyon (FR)

(73) Assignee: Medicrea International, Neyron (FR)

( * ) Notice: Subject to any disclaimer, the term of this patent is extended or adjusted under 35 U.S.C. 154(b) by 478 days.

(21) Appl. No.: 12/922,281

(22) PCT Filed: Mar. 25, 2009

(86) PCT No.: PCT/IB2009/051237
§ 371 (c)(1),
(2), (4) Date: Sep. 24, 2010

(87) PCT Pub. No.: WO2009/118692
PCT Pub. Date: Oct. 1, 2009

(65) Prior Publication Data
US 2011/0015679 A1    Jan. 20, 2011

(30) Foreign Application Priority Data
Mar. 25, 2008  (FR) .................... 08 01596

(51) Int. Cl.
*A61B 17/70*  (2006.01)
*A61B 19/00*  (2006.01)

(52) U.S. Cl.
CPC ......... *A61B 17/7001* (2013.01); *A61B 17/7047* (2013.01); *A61B 17/7041* (2013.01); *A61B 2019/307* (2013.01); *A61B 17/7035* (2013.01); *A61B 17/7007* (2013.01)
USPC ....................................... 606/276

(58) Field of Classification Search
CPC ........... A61B 17/7035; A61B 17/7041; A61B 17/7047; A61B 17/7007
USPC .......... 606/250–253, 258, 276–278, 324, 330
See application file for complete search history.

(56) References Cited

U.S. PATENT DOCUMENTS 5,380,325 A * 1/1995 Lahille et al. ................. 606/250
5,522,816 A * 6/1996 Dinello et al. ................ 606/252

(Continued)

FOREIGN PATENT DOCUMENTS

| EP | 0 446 092 A1 | 9/1991 |
| FR | 2 767 263 | 2/1999 |
| FR | 2 816 196 | 5/2002 |

OTHER PUBLICATIONS

Written Opinion of the International Searching Authority issued in International Patent Application No. PCT/IB2009/051237 dated Jun. 3, 2009.

(Continued)

*Primary Examiner* — Jan Christopher Merene
*Assistant Examiner* — Atiya Mahmud
(74) *Attorney, Agent, or Firm* — Oliff PLC

(57) ABSTRACT

This equipment comprises at least one anchoring assembly including two antagonistic hooks connected to each other through a rod, a first of these hooks having a body crossed by a hole for letting through the rod and being able to be connected to connection means with which the anchoring assembly may be connected to another part of the equipment; said body has an aperture laid out substantially perpendicularly to the axis of said hole, communicating with this hole, and the anchoring assembly has a tightening member which may be engaged into this aperture until it abuts against the rod engaged in the hole, and tightened in order to immobilize this rod in this hole. Said tightening member is directly connected to a part belonging to said connection means, which allows the mounting of the latter on the body of said first hook.

11 Claims, 2 Drawing Sheets

(56) References Cited

U.S. PATENT DOCUMENTS

| | | | |
|---|---|---|---|
| 5,527,314 A * | 6/1996 | Brumfield et al. | 606/278 |
| 5,591,166 A * | 1/1997 | Bernhardt et al. | 606/266 |
| 5,984,924 A * | 11/1999 | Asher et al. | 606/264 |
| 6,050,997 A * | 4/2000 | Mullane | 606/250 |
| 6,069,039 A * | 5/2000 | Lee et al. | 438/258 |
| 6,077,263 A | 6/2000 | Ameil et al. | |
| 6,096,039 A | 8/2000 | Stoltenberg et al. | |
| 6,267,765 B1 * | 7/2001 | Taylor et al. | 606/86 A |
| 6,554,831 B1 * | 4/2003 | Rivard et al. | 606/253 |
| 6,887,242 B2 * | 5/2005 | Doubler et al. | 606/274 |
| 7,033,358 B2 * | 4/2006 | Taylor et al. | 606/277 |
| 7,628,799 B2 * | 12/2009 | Richelsoph et al. | 606/250 |
| 2002/0169451 A1 * | 11/2002 | Yeh | 606/61 |
| 2004/0006342 A1 * | 1/2004 | Altarac et al. | 606/61 |
| 2004/0260285 A1 * | 12/2004 | Steib et al. | 606/61 |
| 2005/0010215 A1 * | 1/2005 | Delecrin et al. | 606/61 |
| 2006/0217718 A1 * | 9/2006 | Chervitz et al. | 606/61 |
| 2007/0072493 A1 * | 3/2007 | Sournac et al. | 439/715 |
| 2007/0173817 A1 * | 7/2007 | Sournac et al. | 606/61 |
| 2007/0213723 A1 * | 9/2007 | Markworth et al. | 606/61 |
| 2008/0114401 A1 * | 5/2008 | Liu et al. | 606/276 |

OTHER PUBLICATIONS

International Search Report in International Application No. PCT/IB2009/051237, dated Jun. 3, 2009.

* cited by examiner

VERTEBRAL ARTHRODESIS EQUIPMENT

The present invention relates to a vertebral arthrodesis equipment.

Such a piece of equipment generally comprises one or two binding bars with which a series of vertebrae may be bound together, and assemblies for anchoring these binding bars to the vertebrae, with hooks or with pedicular screws. This piece of equipment may also comprise crossbars which transversely connect two binding bars step by step in order to maintain them together.

An existing type of anchoring assembly comprises two antagonistic hooks connected to each other through a rod, a first hook of which comprises a body crossed by the rod and is connected to means for connecting to a binding bar. In the anchoring assembly known from French patent application No. FR 2 816 196, in the name of the applicant, said body of the first hook comprises a hole for letting through the rod, this hole having an oblong section on the side turned towards the second hook; this oblong section of the hole allows the rod to be shifted in a plane and therefore increases the possibilities of positioning this second hook relatively to the first hook. The rod is threaded and after having crossed the body of the first hook, receives a nut with which it may be connected to the first hook. By tightening this nut, the second hook may be brought closer to the first hook.

This known piece of equipment gives satisfaction in practice but however it may be improved. Indeed, the nut may, depending on the position of the anchoring assembly on the vertebrae, be more or less difficult to access, making the tightening operation of this nut delicate. Further, any risk of loosening of the anchoring assembly relatively to the vertebrae is not excluded with this piece of equipment.

Document FR 2 767 263 describes an anchoring assembly including two antagonistic hooks connected to each other through a rod; a first of these hooks comprises a body crossed by a conduit for letting through the rod and is able to receive a screw for tightening this rod in this conduit; said body comprises a second conduit, for receiving a bar for binding a series of vertebrae, and is able to receive a nut with which this bar may be connected to the anchoring assembly.

With this equipment; it is not possible to find a remedy to the aforementioned drawbacks. The risk of losing the screw when placing it, is noteworthy and it further has a complex structure to be made.

The object of the present invention is to provide an anchoring assembly finding a remedy to the drawbacks mentioned above.

The relevant piece of equipment comprises in a way known per se, at least one anchoring assembly including two antagonistic hooks connected to each other through a rod, a first of these hooks comprising a body crossed by a hole for letting through the rod and being able to be connected to connection means with which the anchoring assembly may be connected to another part, which the piece of equipment comprises, in particular to a bar for binding a series of vertebrae; said body comprises an aperture laid out substantially perpendicularly to the axis of said hole, communicating with this hole, and the anchoring assembly comprises a tightening member which may be engaged into this aperture until it abuts against the rod engaged in the hole, and tightened in order to immobilize this rod in this hole.

According to the invention, said tightening member is directly connected to a part belonging to said connection means, which allows the mounting of the latter on the body of said first hook.

Thus, in a piece of equipment according to the invention, the tightening member intended to immobilize the rod is not mounted on the end of the rod jutting out from the body of this hook but is placed directly in the body of the hook, so as to bear against the rod and to tighten the latter against the body of the hook. This tightening member is easily accessible regardless of the position of the anchoring assembly relatively to the treated vertebrae, which notably facilitates placement of this anchoring assembly on these vertebrae and with which perfect immobilization of the rod may be achieved relatively to said first hook.

With the tightening member, it is further possible, and especially because it is directly connected to a part belonging to said connection means, to easily perform the mounting of this part on the body of said first hook.

The making of the anchoring assembly according to the invention and its placement on the vertebrae are thereby facilitated.

The part to which the tightening member is connected may be integral with this tightening member, i.e. not jointed relatively to this tightening member. Such a non-jointed part is generally said to be "monoaxial". In this case, said tightening member is advantageously formed by a portion of this part, integral with the latter.

The part to which the tightening member is connected may be also be jointed relatively to this tightening member, such a jointed part is generally said to be "polyaxial". In this case, said tightening member is formed by a binding part independent of said part, connected in a jointed way to the latter.

Preferably,
  the rod comprises at least one first flat at its portion intended to be engaged into said hole, and
  said tightening member comprises a flat face intended to bear against this first flat of the rod.

This flat and this flat surface allow the tightening member to bear against the rod according to a relatively extended surface area, providing good immobilization of the rod relatively to the tightening member.

Advantageously, the rod has a second flat on its face opposite to the one comprising said first flat and the body of said first hook comprises flat surfaces intended to receive this second flat when the rod is engaged into said hole.

Extended contact surface areas are thereby laid out between the rod and the body of the hook providing a good support of these rods against this hook and allowing the existence of friction favorable to proper immobilization of the rod relatively to the body of the hook when the tightening member is tightened.

The rod and/or the body of said first hook and/or said tightening member may comprise at least one rough surface at their contact areas, able to oppose the sliding of the rod relatively to the tightening member when this member is tightened. The roughness of this surface may notably result from knurling.

According to a preferred embodiment of the invention,
  said aperture laid out in the body is formed by a tapped bore, and
  said tightening member comprises a threaded portion allowing it to be screwed into this tapped bore.

When the anchoring assembly comprises a polyaxial assembling part, said anchoring member includes this threaded portion and comprises a gripping area by which it may be grasped in order to screw it in to the tapped bore.

The invention will be better understood and other features and advantages thereof will become apparent, with reference to the appended schematic drawing illustrating as a nonlimiting example, a preferred embodiment of an anchoring system which the piece of equipment comprises, and to which it is related.

Figure 1:
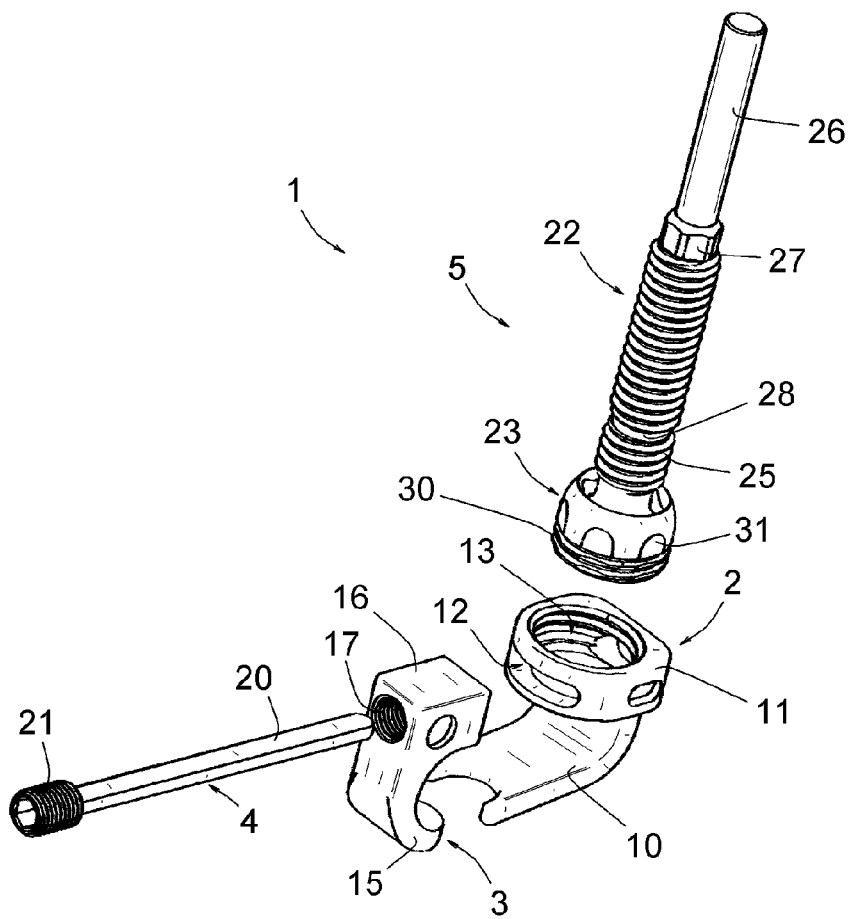
FIG. 1 is an exploded perspective view of the different parts forming this assembly.
Figure 2:
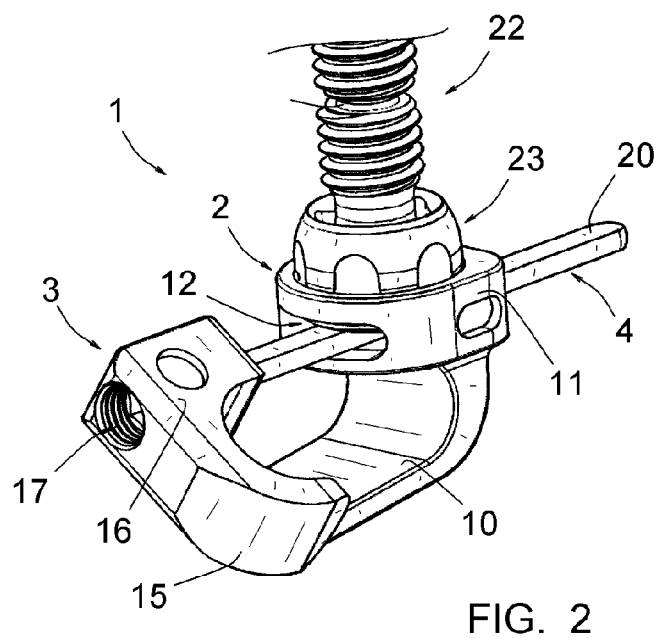
FIG. 2 is a perspective view of this assembly in the mounted condition.
Figure 3:
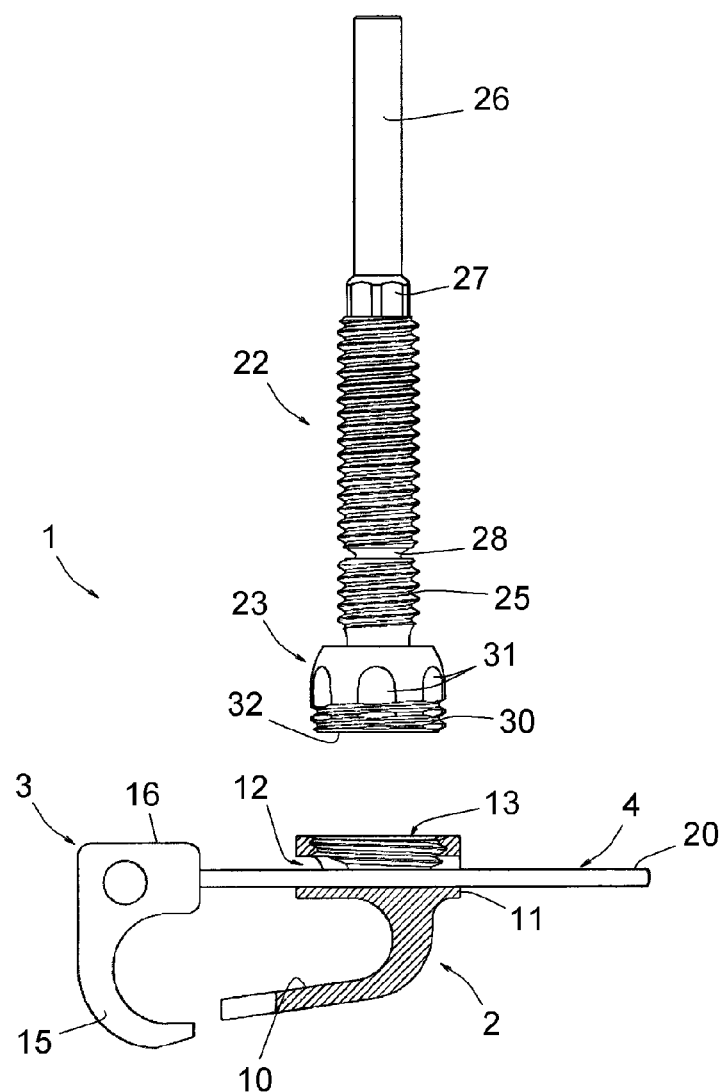
FIG. 3 is a side view of this assembly, during assembling, a first hook which this assembly comprises being seen as a sectional view.
Figure 4:
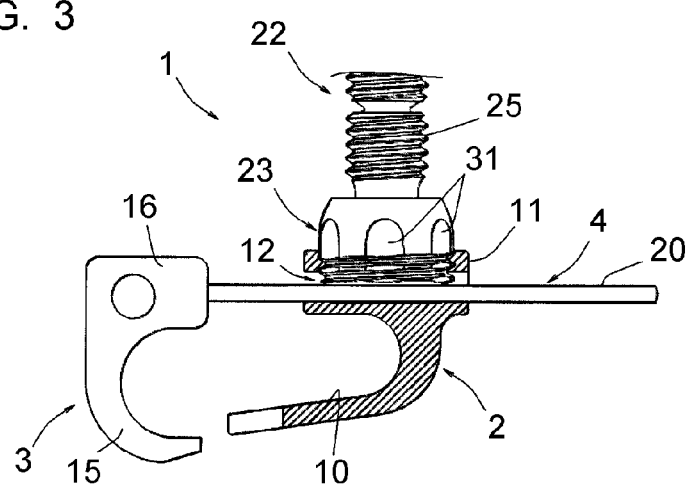
FIG. 4 is a view of the assembly similar to FIG. 3 after assembling.

The figures illustrate an anchoring assembly 1 belonging to a piece of vertebral arthrodesis equipment.

This vertebral arthrodesis equipment comprises, as this is well-known, one or two binding bars with which a series of vertebrae may be bound together and several assemblies 1 allowing these binding bars to be anchored to the vertebrae. This piece of equipment may also comprise crossbars which transversely connect two binding bars step by step in order to maintain them together.

Said bars and cross bars are well-known per se and are therefore not illustrated in the drawings, nor particularly described.

As shown by the figures, an anchoring assembly 1 comprises a first hook 2, a second hook 3, positioned in an antagonistic way to the first hook 2, a rod 4 for connecting both of these hooks 2, 3 and a connection sub-assembly 5. Both hooks 2, 3 are intended to be simultaneously engaged around bone areas of a vertebra, notably at the lamina so that this assembly 1 may be connected to this vertebra.

The assembly 1 may notably be made in a biocompatible metal such as titanium or titanium alloy.

The first hook 2 has a bent branch 10 for bearing against the vertebra and a body 11. This body 11 comprises a hole 12 which passes right through it, in which the rod 4 is intended to be engaged, and a tapped bore 13, extending into the body 11 from the face of this body opposite to the branch 10, until it communicates with the hole 12.

The latter has on the side of the hook 3, as seen along its axis, a flattened oblong shape; on the side opposite to the hook 3, it has a rectangular shape. As this is understood, by means of this shape of the hole 12, the rod 4 may have a sectorial displacement relatively to the first hook 2, in a plane perpendicular to the axis of the bore 13.

The second hook 3 has a bent branch 15 and comprises a body 16 pierced with a tapped bore 17.

The rod 4 comprises two longitudinal flats 20 on both opposite faces, cross-sectionally providing it with a substantially rectangular shape. At its end opposite to the one intended to be engaged into the hole 12, it comprises a threaded cylindrical portion 21 intended to be screwed into the tapped bore 17 of the hook 3.

The connection sub-assembly 5 comprises in the illustrated example a threaded pin 22 and a binding part 23 jointed with each other. This joint is made by means of a terminal spherical portion which the pin 22 comprises, and of a spherical cavity for receiving this terminal portion laid out in the binding part 23. In order to achieve the connection of this pin 22 and of the part 23, the binding part 23 may notably comprise a peripheral wall able to be folded back against the spherical portion of the pin 22 by deformation around this spherical portion, in a crimping fashion.

The pin 22 comprises a threaded portion 25 intended, as this is known, to receive a stirrup for connecting a binding bar as aforementioned, and to then receive a nut for tightening this stirrup around this binding bar; the stirrup resting against the peripheral wall of the binding part 23. This stirrup and this nut, being well-known per se, are not particularly illustrated in the drawings nor described.

The pin 22 also comprises a smooth proximal portion 26 for facilitating the engagement of the stirrup and of the nut on it, a portion 27 with facets allowing this pin 22 to be immobilized in rotation when screwing in said nut, and a portion 28 with a smaller section, able to be broken after tightening the nut against the stirrup.

The binding part 23 is, as this appears in the figures, intended to be screwed into the tapped bore 13. For this purpose it comprises a threaded portion 30 allowing it to be screwed into this bore and a plurality of facets 31 on its periphery allowing it to be gripped by means of a suitable tool and to be driven into rotation. The binding part 23 further comprises a planar distal face 32 intended to bear against the rod 4 when it is screwed into the bore 13.

As this is understood, the anchoring assembly 1 is assembled by engaging the rod 4 through the bore 17 of the hook 3, by screwing the threaded portion 21 into this bore, by engaging the rod 4 into the hole 12 and by then screwing the binding part 23 into the tapped bore 13 without tightening.

The assembly 1 provides many possibilities for placement on a vertebra because of the possibility of pivoting the hook 3 relatively to the rod 4, and of the possibility of sectorial displacement and sliding of this rod 4 through the body 11 of the hook 2.

Once the assembly 1 is placed on the vertebra, the binding part 23 is tightened by means of a suitable tool so as to immobilize the rod 4 relatively to the hook 2. This immobilization is achieved by extended contact areas resulting from the flats 20 of the rod 4, from areas of the body 11 delimiting the apertures through which the hole 12 opens out on the outside of this body 11 and the end planar face 32 of the binding part 23. Perfect immobilization of the rod 4 relatively to the hook 2 is thereby obtained, and the binding part 23 remains easily accessible regardless of the position of the anchoring assembly 1 relatively to the treated vertebrae, which notably facilitates the placement of this anchoring assembly on these vertebrae.

Further, the risk of pivoting of the rod 4 on itself is eliminated by said flat 20 and the binding part 23.

The invention therefore provides a piece of vertebral arthrodesis equipment having the determining advantages of allowing perfect immobilization of the assembly 1 in the mounting position, while having a setting into place which remains relatively easy.

The invention has been described above with reference to an embodiment given as a pure example. It is obvious that it is not limited to this embodiment but that it extends to all other embodiments covered by the appended claims herein.

The invention claimed is:

1. Vertebral arthrodesis equipment, comprising
one binding bar with which a series of vertebrae are capable to be bound together; and
at least one anchoring assembly including
two antagonistic hooks configured to be simultaneously engaged around bone areas of a vertebra, the hooks being configured to be connected to each other by a rod, a first one of the hooks comprising a bent branch and a body, the body being crossed by a hole for letting through the rod, the body comprising a tapped bore laid out substantially perpendicular to an axis of the hole, the tapped bore communicating with the hole, and the tapped bore extending into the body from the face of the body opposite to the branch;

a threaded pin configured to connect to one of the binding bars, and to be connected to the first hook, the threaded pin being connected to a threaded binding part adapted to be screwed into the tapped bore until the threaded binding part abuts the rod engaged in the hole, and tightened such that the rod is immobilized in the hole, wherein the threaded pin is jointly connected to the threaded binding part.

2. Equipment according to claim 1, wherein:
the rod comprises at least one first flat face at a portion of the rod intended to be engaged into the hole, and
the threaded binding part comprises a flat face intended to bear against the at least one first flat face of the rod.

3. Equipment according to claim 2, wherein the rod further comprises a second flat face on a side opposite the at least one first flat face, and the body of the first hook comprises flat surfaces intended to receive the second flat face when the rod is engaged into the hole.

4. Equipment according to claim 1, wherein the threaded binding part comprises an engagement portion allowing the threaded binding part to be gripped and driven into the tapped bore.

5. Equipment according to claim 4, wherein the hole for letting the rod through the body has
a flattened oblong shape on a side of the body facing a second one of the hooks; and
a rectangular shape on a side of the body opposite the second hook.

6. Equipment according to claim 1, wherein the bent branch is for bearing against a vertebra and the body, the tapped bore extending into the body from a face of the body opposite the bent branch, until the tapped bore communicates with the hole.

7. Equipment according to claim 6 further comprising:
a second hook having a bent branch and a body pierced with a tapped bore,
wherein the rod comprises, at its end opposite an end intended to be engaged into the hole, a threaded cylindrical portion configured to be screwed into the tapped bore of the second hook.

8. Equipment according to claim 1, wherein the rod and/or the body of the first hook and/or the threaded binding part comprises at least one rough surface at their contact areas, able to oppose the sliding of the rod relative to the threaded binding part when the threaded binding part is tightened.

9. Equipment according to claim 1, wherein the threaded binding part comprises an engagement portion allowing the threaded binding part to be gripped and driven into the tapped bore.

10. Equipment according to claim 1, wherein the hook portion is integral with the hook body.

11. Equipment according to claim 1, wherein an axis of the bore intersects a center axis of the hole receiving the rod, such that a cross area of the tapped bore at least substantially intersects the hole receiving the rod.

* * * * *